US00PP19954P3

(12) United States Plant Patent
Meilland

(10) Patent No.: US PP19,954 P3
(45) Date of Patent: Apr. 21, 2009

(54) MINIATURE ROSE PLANT NAMED 'MEIMARIVON'

(50) Latin Name: *Rosa hybrida*
Varietal Denomination: Meimarivon

(75) Inventor: Alain A. Meilland, Antibes (FR)

(73) Assignee: CP Delaware, Inc., Wilmington, DE (US)

( * ) Notice: Subject to any disclaimer, the term of this patent is extended or adjusted under 35 U.S.C. 154(b) by 261 days.

(21) Appl. No.: 11/711,016

(22) Filed: Feb. 27, 2007

(65) Prior Publication Data

US 2008/0209599 P1 Aug. 28, 2008

(51) Int. Cl.
*A01H 5/00* (2006.01)

(52) U.S. Cl. ..... Plt./121
(58) Field of Classification Search ..... Plt./121
See application file for complete search history.

*Primary Examiner*—Kent L Bell
(74) *Attorney, Agent, or Firm*—Buchanan Ingersoll & Rooney PC

(57) ABSTRACT

A new and distinct Miniature rose plant is provided which abundantly forms on a substantially continuous basis attractive pink blossoms. A low and compact growth habit is displayed that is well adapted for pot culture. The dense glossy green foliage contracts nicely with the pink blossom coloration. The tolerance to diseases is very good, particularly with respect to Oidium.

1 Drawing Sheet

Figures 1, 2, 3, 4, 5, 6, 7, 8, 9, 10, 11, 12, 13, 14, 15, 16, 17:
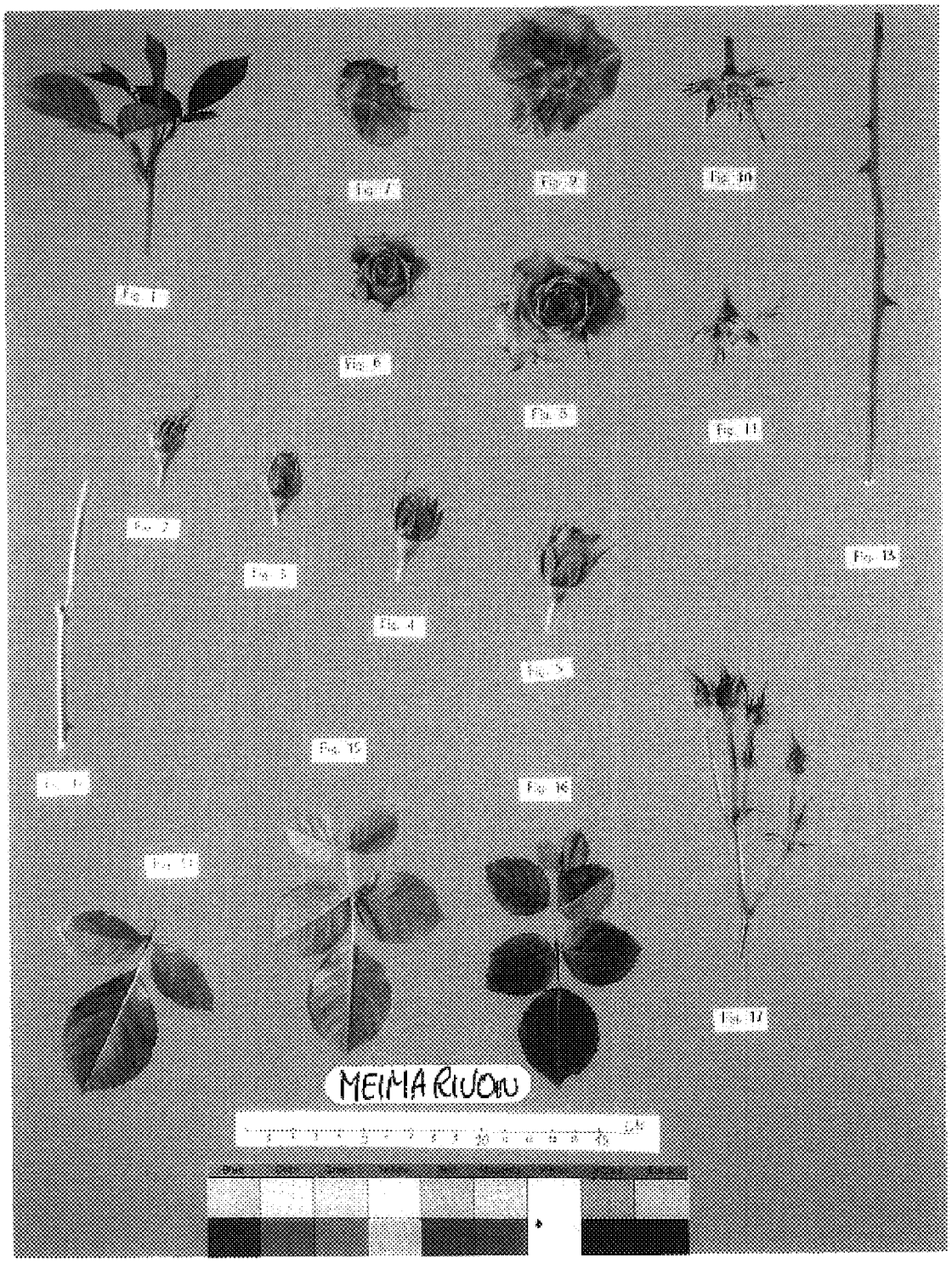

Botanical/commercial classification: *Rosa hybrida*/Miniature Rose Plant.
Varietal denomination: cv. Meimarivon.

SUMMARY OF THE INVENTION

The new variety of *Rosa hybrida* Miniature rose plant was created by artificial pollination wherein two parents were crossed which previously had been studied in the hope that they would contribute the desired characteristics. The female parent (i.e., the seed parent) of the new variety was the product of the cross of the 'Meichanso' variety (non-patented in the United States) and the 'Ruimired' variety (U.S. Plant Pat. No. 5,770). The male parent (i.e., the pollen parent) was the 'Savaje' variety (non-patented in the United States). The parentage of the new variety can be summarized as follows:

('Meichanso'×'Ruimired')×'Savaje'.

The seeds resulting from the above pollination were sown and small plants were obtained which were physically and biologically different from each other. Selective study resulted in the identification of a single plant of the new variety.

It was found that the new variety of Miniature rose plant of the present invention displays the following combination of characteristics:

(a) exhibits a compact and low growth habit that is well adapted for pot culture, (b) abundantly forms on a substantially continuous basis attractive pink blossoms, and (c) forms attractive dense glossy green foliage.

The new variety well meets the needs of the horticultural industry. It is particularly well suited for growing in pots as well as in the landscape. For instance, it can be grown to advantage along walkways and in mixed border plantings. The glossy green foliage contrasts well with the pink blossom coloration.

The new variety has been found to undergo asexual propagation in France by a number of routes, including budding, grafting, and cuttage. Asexual propagation by the above-mentioned methods as performed in the South of France has shown that the characteristics of the new variety are strictly transmissible from one generation to another.

The new variety of the present invention can be readily distinguished from its ancestors. The flower coloration is different in each instance. More specifically, the 'Meichanso' variety forms Geranium Red flowers, the 'Ruimired' variety forms Orient Red flowers, and the 'Savaje' variety forms yellow flowers.

The new variety has been named 'Meimarivon'.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were six months of age and were observed during May while growing outdoors on their own roots at LeCannet des Maures, Var, France. Dimensions in centimeters are shown at the bottom of the photograph.

FIG. 1—illustrates a specimen of a young shoot;

FIG. 2—illustrates a specimen of a floral bud before the opening of the sepals;

FIG. 3—illustrates a specimen of a floral bud at the opening of the sepals;

FIG. 4—illustrates a specimen of a floral bud at the opening of the petals;

FIG. 5—illustrates a specimen of a flower during the course of opening;

FIG. 6—illustrates a specimen of an open flower-plan view-obverse;

FIG. 7—illustrates a specimen of an open flower-plan view-reverse;

FIG. 8—illustrates a specimen of a fully open flower-plan view-obverse;

FIG. 9—illustrates a specimen of a fully open flower-plan view-reverse;

FIG. 10—illustrates a specimen of a floral receptacle showing the arrangement of the stamens and pistils;

FIG. 11—illustrates a specimen of a floral receptacle showing the arrangement of the pistils (stamens removed);

FIG. 12—illustrates a specimen of a flowering stem;

FIG. 13—illustrates a specimen of a main branch;

FIG. 14—illustrates a specimen of a leaf with three leaflets-plan view-upper surface;

FIG. 15—illustrates specimen of a leaf with five leaflets-plan view-under surface;

FIG. 16—illustrates a specimen of a leaf with seven leaflets-plan view-upper surface; and FIG. 17—illustrates a cluster of buds.

DETAILED DESCRIPTION

The chart used in the identification of the colors is that of The Royal Horticultural Society (R.H.S. Colour Chart). The description is based on the observation of six month-old specimens of the new variety which were observed during May while growing on their own roots outdoors at LeCannet des Maures, Var, France.

Class: Miniature.

Plant:

*Height.*—Approximately 25 to 30 cm on average at the end of the growing season.

*Width.*—Approximately 25 to 30 cm on average at the end of the growing season.

*Habit.*—Compact and bushy.

Branches:

*Color.*—Young stems: near Green Group 138A. Adult wood: near Green Group 138A.

*Thorns.*—Size and quantity: on young stems approximately 3 on average having a length of approximately 0.5 cm and approximately 1 on average having a length of approximately 0.2 cm over a length of 10 cm, and on adult stems approximately 8 on average having a length of approximately 0.5 cm and approximately 1 on average having a length of approximately 0.3 cm over a length of 10 cm. Color: on young stems near Greyed-Orange Group 176A, and on adult stems near Greyed-Orange Group 177B. Configuration: very elongated and curved downwards on the upper surface and slightly concave to concave on the under surface, and with an oval and narrow base.

Leaves:

*Petioles.*—Upper surface: non-glandular, and near Green Group 137B in coloration. Under surface: bear a very few prickles, and near 137D in coloration. Size: approximately 3.2 cm in length on average on the terminal leaflet.

*Rachis.*—Upper surface: near Green Group 137B in coloration. Under surface: near Green Group 137D in coloration.

*Stipules.*—Adnate, pectinate, narrow, smooth, approximately 1.7 cm in length on average, approximately 0.2 cm in width on average, near Green Group 139A on the upper surface, and near Green Group 137C on the under surface.

*Leaflets.*—Number: 3, 5 (most often), and 7. Shape: elliptical, with a pointed tip and an obtuse base (as illustrated). Texture: rather thick. Serration: small and single. General appearance: very dense, medium green, and glossy. Size: terminal leaflets commonly measure approximately 4.7 cm in length on average and approximately 3.2 cm in width on average. Color (young foliage): Upper surface: near Yellow-Green Group 144A and bordered with Greyed-Orange Group 176A. Under surface: near Greyed-Green Group 191A. Color (mature foliage): Upper surface: near Yellow-Green Group 147A. Under surface: near Green Group 138B.

Inflorescence:

*Number of flowers.*—Commonly approximately 1 to 5 flowers per stem, commonly in clusters.

*Peduncle.*—Glandular, near Yellow-Green Group 144A in coloration, approximately 1.4 cm in length on average, and approximately 0.3 cm in diameter on average.

*Sepals.*—Upper surface: tomentose, and near Yellow-Green Group 146C in coloration. Under surface: tomentose, and near Yellow-Green Group 144A in coloration. Shape: longish-pointed at the tip, incurved at the base, and commonly bear some weak foliaceous extensions. Length: approximately 2.3 cm on average. Width: approximately 0.6 cm on average.

*Buds.*—Shape: conical. Size: small, approximately 2.3 cm in length on average, and approximately 1.9 cm in width on average. Color: as the calyx breaks on the upper surface near Red-Purple Group 58C and more or less suffused with Red-Purple Group 58B, and on the under surface near Red-Purple Group 58C and widely suffused with near Red-Purple Group 58A and 58B, and with a small spot of Yellow-Green Group 149C at the base.

*Flower.*—Form: double and flat cup-shaped. Diameter: approximately 4 cm on average when fully open. Color (during the course of opening): Upper surface: near Red-Purple Group 58D, more or less suffused with Red-Purple Group 58C, and with a small spot of Yellow-Green Group 154D at the base. Under surface: near Red-Purple Group 58D, widely suffused with Red-Purple Group 58C, and with a small spot of Yellow-Green Group 154D at the base. Color (when open): Upper surface: near Red-Purple Group 154D, more or less suffused with Red-Purple Group 58C, and with a small spot of Yellow-Green Group 154D at the base. Under surface: near Red-Purple Group 58D, widely suffused with Red-Purple Group 58C, and with a small spot of Yellow-Green Group 154D at the base. Discoloration: very slight with age. Fragrance: none. Anthers: near Greyed-Orange Group 163B in coloration, regularly arranged around the styles, and approximately 0.2 cm in size on average. Stamen number: approximately 94 on average. Filaments: near Greyed-Yellow Group 16B in coloration, and approximately 0.5 cm in length on average. Pistil number: approximately 78 on average. Stigmas: near Green-White Group 157A in coloration, and approximately 0.8 cm in size on average. Styles: near Green-Yellow Group 1C in coloration, and approximately 0.1 cm in length. Petal number: approximately 64 on average under normal growing conditions. Petal arrangement: imbricated. Petal shape: possess an obtuse base and a rounded tip. Petal size: approximately 2.5 cm in length on average, and approximately 2.5 cm in width on average. Petal texture: flexible. Petal drop: good, the petals commonly detach cleanly before drying. Petaloids: none observed. Receptacle: commonly tomentose, near Yellow-Green Group 144A in coloration, funnel-shaped in cross section, and approximately 1.4 cm in length on average and approximately 0.3 in width on average. Hips: none observed. Lasting quality: approximately two weeks on the plant on average.

Development:

*Vegetation.*—Strong.

*Blooming.*—Abundant and substantially continuous.

*Tolerance to diseases.*—Very good, especially with respect to Oidium.

*Aptitude to bear fruit.*—None observed during observations to date.

I claim:

1. A new and distinct variety of Miniature rose plant characterized by the following combination of characteristics:

(a) exhibits a compact and low growth habit that is well adapted for pot culture, (b) abundantly forms on a substantially continuous basis attractive pink blossoms, and (c) forms attractive dense glossy green foliage;

substantially as herein shown and described.

* * * * *

MEIMA RIJON